United States Patent [19]
Tippins et al.

[11] Patent Number: 5,888,369
[45] Date of Patent: Mar. 30, 1999

[54] APPARATUS FOR CONDUCTING ELECTROPHORESIS EXPERIMENTS

[75] Inventors: Barbara L. Tippins, Temecula; Roumen Bogoev, Escondido; Douglas R. Levy, Carlsbad, all of Calif.

[73] Assignee: Novel Experimental Technology, San Diego, Calif.

[21] Appl. No.: 828,398

[22] Filed: Mar. 28, 1997

[51] Int. Cl.⁶ .................................................. G01N 27/22
[52] U.S. Cl. ..................... 204/606; 204/456; 204/466; 204/467; 204/616; 204/621
[58] Field of Search ................... 204/456, 457, 204/466, 467, 606, 607, 616, 618, 621

[56] References Cited

U.S. PATENT DOCUMENTS 5,158,661  10/1992  Hansen ................................. 204/299 R

OTHER PUBLICATIONS

Hongyo, T., et al., "Cold SSCP': A Simple, Rapid and Non–radioactive Method for Optimized Single–Strand Conformation Polymorphism Analysis", Nucleic Acids Research, vol. 21, No. 16, 3637–3642 (1993).
Yoshimoto, H.I.., et al, "Multiple Fluorescence–Based PCR–SSCP Analysis", Biotechniques, 16, 296–306 (1994).
Instruction Manual for C.B.S. Scientific Company, Inc.,'s Denaturing Gradient Gel Electrophoresis System (1994).
DNA Sequencing Guide, United States Biochemical Corporation, Gel Electrophoresis Section (Date Unknown).
BioTherm Corporation, sales literature for "Cool Gel" Mini Apparatus (1994).
Integrated Separation Systems, sales literature for "Maxi 2–Gel Device" with built–in cooling coil (1994).
Owl Scientific,Inc., sales literature, "Penguin" P8DS–1, P9DS–1, and P10DS–1, Water Cooled Dual Gel System.
Stratagene, sale literature, "StrataTherm Cold Temperature Controller and Feathervolt Power Supply", (1994).
Bio–Rad, sales literature, "Sequi–Gen II Sequencing Cell." (1994).
Hoefer, sales literature, "Mighty Small II Dual Cooled Vertical Slab Unit."
Fotodyne, sales literature, "Buffer Cooler/Circulator and Vertical Cell II Air Cooled Chamber."

Primary Examiner—David R. Redding
Attorney, Agent, or Firm—Dain & Li LLP; Kam W Li

[57] ABSTRACT

An apparatus of conducting electrophoresis experiments including a container for receiving an electrophoresis buffer and a buffer core assembly for holding gel-containing cassettes that are immersed in the buffer for molecular separation of an electrophoresis sample. The buffer core assembly defines a flow path for the electrophoresis buffer which can be circulated by means of a heat exchanger and a pump to effect controlled heat exchange between the buffer and the cassette surfaces thereby maintaining the gel and the electrophoresis process at a desirable temperature uniformly over the surfaces of the gel cassette. The buffer core assembly also has upper well for receiving a second electrically chargeable buffer in contact with the gel so as to impose an electric field on the gel for the electrophoresis in conjunction with the first buffer. The well is isolated from the first buffer to prevent mixing of the buffers and to reduce the risk of an electrical short.

13 Claims, 4 Drawing Sheets

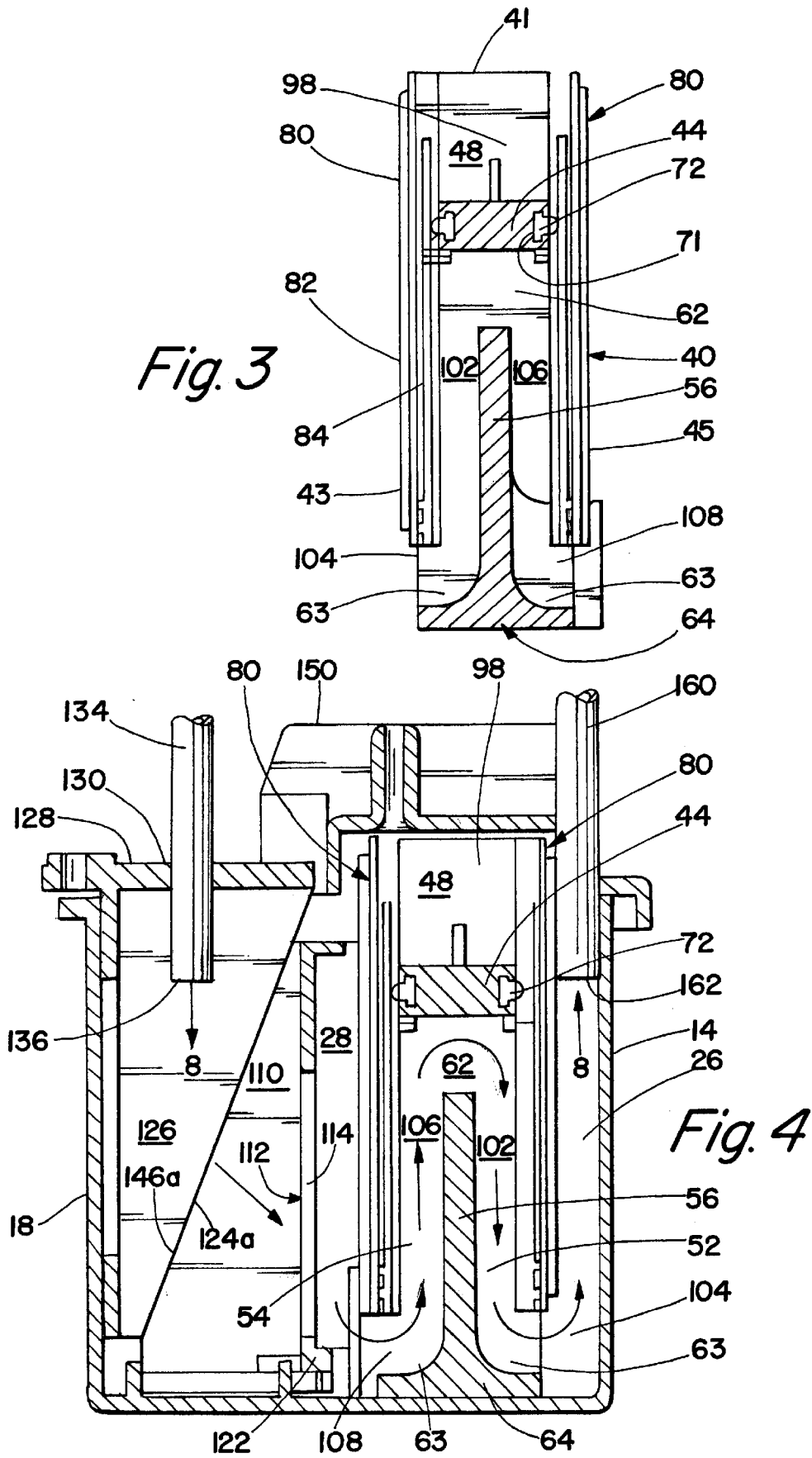

APPARATUS FOR CONDUCTING ELECTROPHORESIS EXPERIMENTS

FIELD OF THE INVENTION

This invention relates to an apparatus for performing electrophoresis experiments and the process of electrophoresis separation. More particularly, this invention relates to a novel system for gel electrophoresis at controlled and reproducible temperatures.

BACKGROUND OF THE INVENTION

Gel electrophoresis is a common procedure for the separation of biological molecules, such as DNA, RNA, and proteins. In gel electrophoresis, the molecules are separated into bands according to the rate at which an imposed electric field causes them to migrate through a filtering gel.

The basic apparatus used in this technique consists of a gel enclosed in a glass tube or sandwiched as a slab between glass or plastic plates. The gel has an open molecular network structure, defining pores which are saturated with an electrically conductive buffered solution of a salt. These pores through the gel are large enough to admit passage of the migrating molecules.

The gel is placed in contact with buffer solutions which make electrical contact between the gel and the cathode or anode of an electrical power supply. A sample containing the macromolecules and a tracking dye is placed on top of the gel. An electric potential is applied to the gel causing the sample macromolecules and tracking dye to migrate toward the bottom of the gel. The locations of the bands of separated macromolecules are then determined. By comparing the distance moved by particular bands in comparison to the tracking dye and macromolecules of known mobility, the mobility of sample macromolecules can be determined. Once the mobility of the sample macromolecules is determined, the size of the macromolecule can be calculated.

As more electrophoretic applications are used in quality control labs and forensic and clinical diagnoses, it is critical to be able to replicate all experimental conditions in multiple locations and labs, a very important variable being temperature. The application of an electrical field to a gel results in the generation of heat. In general, higher temperatures increase the molecular kinetics, which results in faster migration of macromolecules through the separating gel.

However, without temperature control, gels often exhibit uneven temperatures across the width of the gel resulting in "smile" distortions. Smile distortions occur when bands migrate faster in the middle of the gel than on the sides.

Often, even a small temperature differential between the front and rear plates of the gel, if not mitigated, can cause the resulting bands to slant front to back, depending on the thickness of the gel and the heat transfer properties of the cassette plates. This challenge is particularly acute in test runs where the molecular migration rates exhibit overly temperature sensitive characteristics, as in DNA sequencing. For such runs, even a slight temperature differential, e.g. of 0.1° C. can cause the slanted bands to appear overlapping.

Additionally, overheating of the gel (>60° C.) can result in deleterious effects such as breakdown of the gel matrix resulting in poor resolution and band shape, alteration of the macromolecules including denaturation, alkylation or oxidation, and/or damage to the electrophoresis apparatus itself.

In DNA sequencing, electrophoresis is conducted at high voltage (1200–3000 volts, 55 watts) to maintain a gel temperature of 45°–50° C. for maximum resolution of the denatured DNA strands. The temperature is controlled by the amount of power applied to the gel. Gels run too cool (<40° C.) will have bands that are blurred, perhaps due to incomplete denaturation. Gels run too warm (>60° C.) will lose resolution, perhaps due to the breakdown of the polyacrylamide.

Precise temperature control is particularly critical in Single Stranded Conformational Polymorphism (SSCP) analysis of DNA, where bands are extremely close together. The relative temperature differential between the front and the back surfaces of the gel therefore can have a critical effect on the resolution of the DNA bands. For reliable, reproducible results, the gel temperature must be consistent for the duration of the run and in all areas of the gel, and variations of less than 0.1° C. temperature differential between the front and the back surfaces of the gel are required.

Various means have been used to attempt to control the temperature of the gel during electrophoresis. These include applying active or passive heat sinks to one side of the gel, regulating power to the gel, employing an enclosed heat exchanger internal one of the buffer chambers, immersing the gels in a buffer-filled tank containing a heater/circulator, circulating the buffer through tubing immersed in an ice water bath, and circulating the buffer through an external metal heat exchanger.

These means are limited in their ability to provide compact apparatus for maintaining consistent and uniform thermal control across the area encompassing the front and back of the electrophoresis gels. The heat sinks exchange heat on only one side of the gel; the regulation of power to the gels cannot control regional hot spots and obviously limits the application of high wattage to the gels; the internal heat exchanger again exchanges heat on only one side of the gel and does not actively circulate buffer, resulting in vertical thermal gradients within the buffer chamber; immersing the gels in a heater tank is cumbersome, in that it requires a large volume of buffer and cannot cool the gels; and circulating the buffer through tubing immersed in an ice water bath is also cumbersome, and makes difficult fine control of temperature. Circulating the buffer through an external metal heat exchanger provides the most satisfactory temperature control. However, with the current electrophoresis systems, two pumps and heat exchangers would be required to assure uniformity of temperature and separation of the buffer fluids between the cathode and anode chambers. Further, with current electrophoresis systems, circulation of buffer within the chambers and across the gels is random and undirected, which may result in vertical and horizontal thermal gradients.

In view of the afore-mentioned deficiencies within the prior art, it is desirable to provide a compact system which requires only one heat exchanger, maintaining separation of the cathode and anode buffers while assuring consistency and uniformity of temperature across the front and the back of the electrophoresis gel.

It is also desirable for an electrophoresis system to provide the means for circulating a single buffer at any selected temperature (3°–80° C.) over multiple gels simultaneously in order to dissipate heat generated by the electrophoresis process and maintain a consistent thermal environment over a substantial portion of the gel surfaces using a single pump and heat exchanger.

It will be further desirable to allow the user to operate multiple temperature controlled electrophoresis units off of a single thermostatted circulating water bath due to the heat exchangers being located external to the bath.

SUMMARY OF THE INVENTION

According to the present invention, an apparatus for conducting electrophoresis experiment is provided. The apparatus is represented by a compact electrophoresis cell system which effects gel electrophoresis at controlled and reproducible temperature levels by way of buffer circulation in and out of the cell system in a defined flow pattern.

The system includes a container for receiving a first electrically chargeable electrophoresis buffer solution. A buffer core is provided which is held immersable in the buffer solution within the container. The buffer core has an upper section containing an upper chamber or well for receiving a second electrophoresis buffer solution that is isolated from the first buffer solution.

The lower section has a front inset, a rear inset and an inset opening below the upper section. A pair of gel cassettes each containing an electrophoresis gel are affixed to the front and back sides of the buffer core body, partially forming part of the peripheral walls of the upper chamber. Each cassette has a top opening such that the gel is in contact with the second buffer solution in the upper chamber.

At the lower section of the body core body, the cassettes enclose the front inset and the rear inset respectively to form a front compartment and a rear compartment which are open to each other through the inset opening. Each of the compartments has a lower opening to permit passage of the first electrophoresis buffer solution through the compartments to develop a defined serpentine flow path when the first buffer solution is passed between the front portion and the rear portion of the container.

In a representative embodiment of the invention, the upper section of the buffer core is generally of a U-shape where the upraised side members of the U-shape, together with the upper portions of the cassettes form the upraised periphery or sides of the upper chamber or well.

In operation, the first and the second buffer solutions are electrically charged to generate an electric field across the top and the bottom portion of the gel for the electrophoresis run. The electrically charged first buffer is circulated into the container by transport means such as a pump at a temperature level that is maintained by appropriate heat exchanger means to pass through the buffer core assembly compartments and establish a heat exchange relationship with the surfaces of the gel cassettes where electrophoresis molecular separation is to take place.

In the representative embodiment, a set of wedge blocks are provided to secure the buffer core and the gel cassette within the container.

The present invention allows both surfaces of the gel cassette to be continuously exposed to the circulating temperature-controlled buffer in a serpentine fashion. The present invention thus provides a compact electrophoresis system which maintains separation of the cathode and anode buffers while assuring consistency and uniformity of temperature across the front and the back of the electrophoresis gel. The invention eliminates the simultaneous use of two heat exchangers, which would otherwise be required to maintain separation of the cathode and anode buffers.

These and other aspects and advantages of the invention will become apparent from the following detailed description, and the accompanying drawings, which illustrate by way of example the features of the invention.

BRIEF DESCRIPTION OF THE DRAWINGS

FIG. 3 is a cross-sectional view of the buffer core body taken from line 3—3 of FIG. 1;

FIG. 4 is a cross-sectional view of the electrophoresis cell assembly taken from line 4—4 of FIG. 1;

DETAILED DESCRIPTION OF A PREFERRED EMBODIMENT

Figure 1:
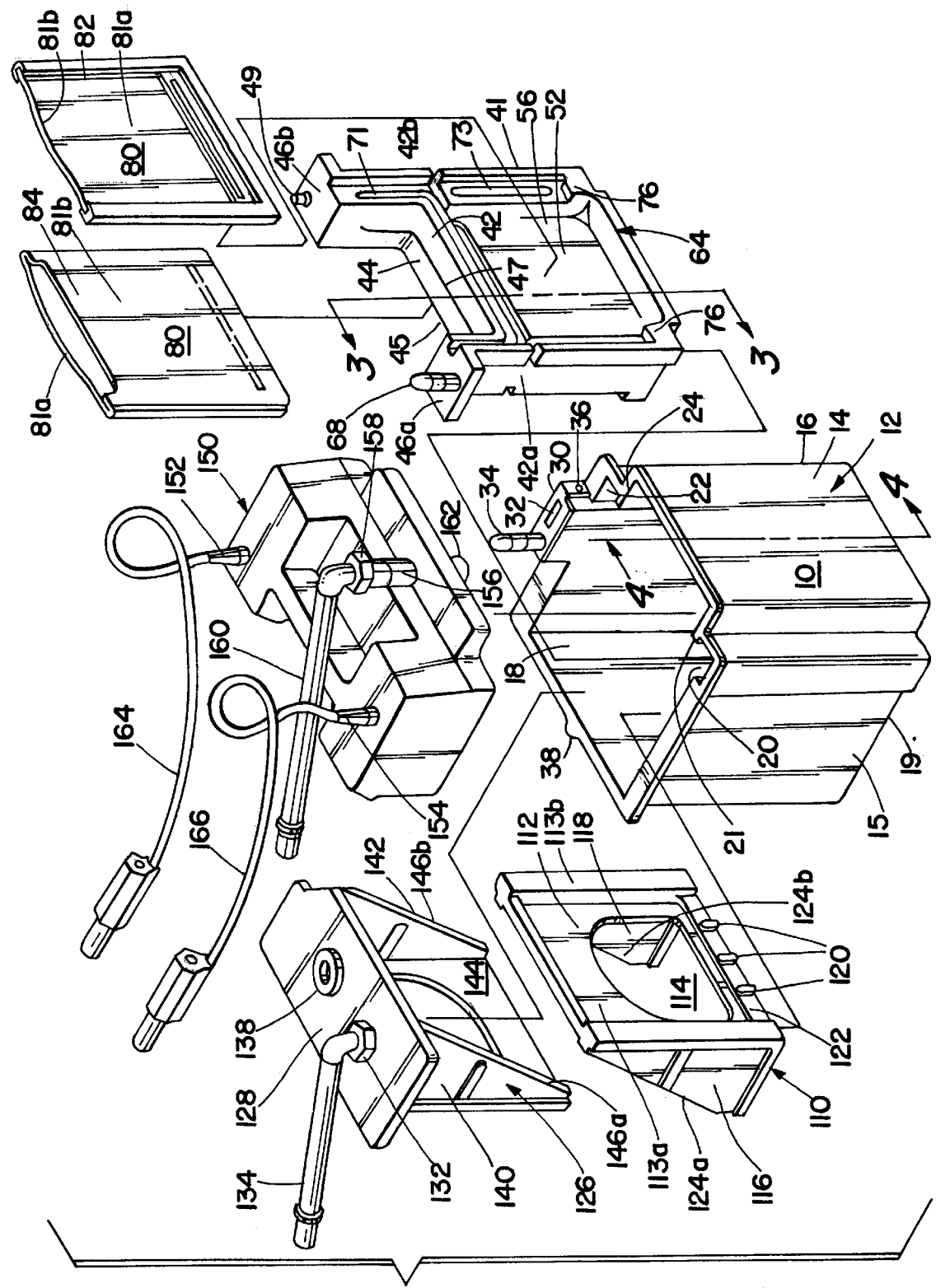
FIG. 1 is an exploded perspective view of the electrophoresis cell assembly of this invention.

The electrophoresis cell system of the invention is a conveniently portable, easily cleanable and highly efficient apparatus for conducting electrophoresis experiments with repetitive results. The electrophoresis cell system representing an exemplary embodiment of the present invention is shown in FIG. 1 in exploded form. The system 10 comprises a container 12, buffer core assembly 40, lower wedge block 110, upper wedge block 126, and a lid 150.

As shown in FIG. 1, container 12 includes a front wall 14, left side wall 15, right side wall 16, back wall 18 and a closed bottom 19. Container 12 is open at the top for receiving a first electrophoresis buffer solution 8.

Mounted by a fastener, such as a screw 36, on the top portion of side wall 16 is an elongated conductor strip 30 having a slot opening 32. A vertical male electrical pole conductor 34 is affixed to conductor strip 30.

Located on the opposite inner surfaces of walls 15 and 16 and spaced away from the front wall 14 of container 12 are wall recesses or channels 20 and 22, having their opening aligned with each other to receive buffer core assembly 40. In the embodiment shown in FIGS. 1–3, wall recesses 20 and 22 are formed integral of left side wall 15 and right side wall 16, respectively. Each of the wall recesses has a cross-section of an irregular C-channel when viewed from the top of container 12.

Wall recesses 20 and 22 are spaced apart at a span that is sufficient to accommodate the lateral width of buffer core assembly 40 and to hold it in place without any significant lateral movement within container 12. The width of wall recesses 20 and 22 is slightly greater than the thickness of buffer core assembly 40 along its lateral sides to facilitate the placement of buffer core assembly 40.

Where wall recesses 20 and 22 they open to the inner side walls 15 and 16 toward the front wall 14 of the container 12, vertical ridges 21 and 24, which run the height of the container, are provided in recesses 20 and 22, respectively, to abut buffer core assembly 40 in its installed position, as will be discussed in further detail below.

Buffer core assembly 40 is slidably installed into wall recesses 20 and 22 from the top of container unit 12, thereby partitioning the container 12 into a front chamber 26 and a rear chamber 28. The lower periphery of the buffer core extends proximally to the bottom 19 of container 12.

The upper portion of the buffer core assembly has a well 48 that is adapted for holding a second electrically chargeable buffer solution, which is isolated from the first buffer 8 in the container 12. In practice, such a well is often referred to as the upper buffer chamber, the anode chamber or the cathode chamber, depending on the polarity of the electrical charge being applied to the buffer contained in the well. In the present description, the term well and upper chamber are used interchangeably.

In the embodiment as shown in FIGS. 1–4, buffer core assembly 40 includes a buffer core body 41 and a pair of gel cassettes 80. The two cassettes are placed on the front side 43 and the back side 45 of buffer core body 41, which partially form a portion of the sides of the well 48.

Figure 2B:
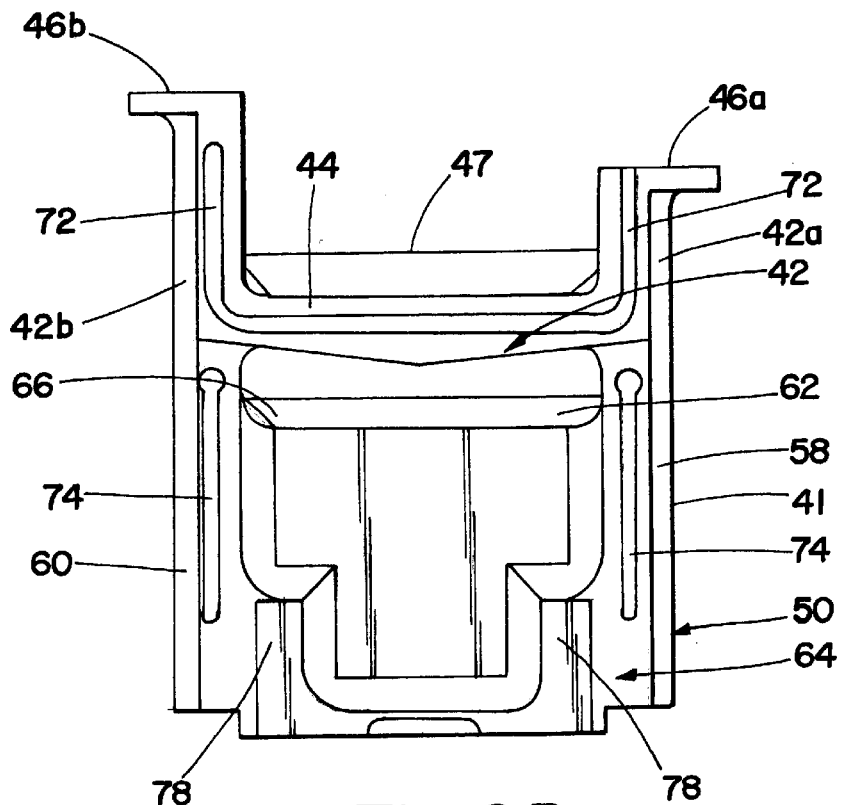
FIG. 2b is a rear elevational view of the buffer core body.
Figure 2A:
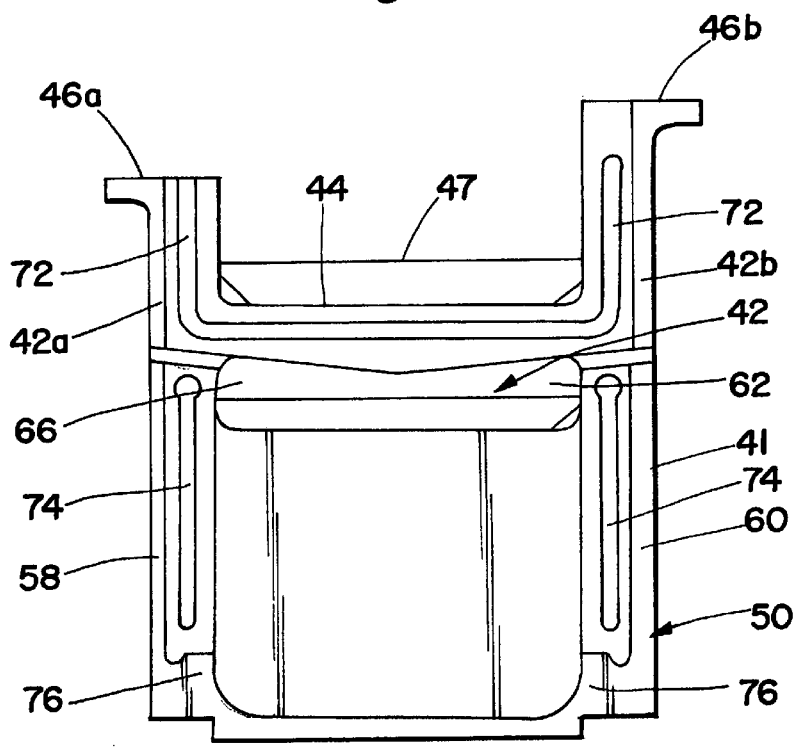
FIG. 2a is a front view of the buffer core body.
Figure 5:
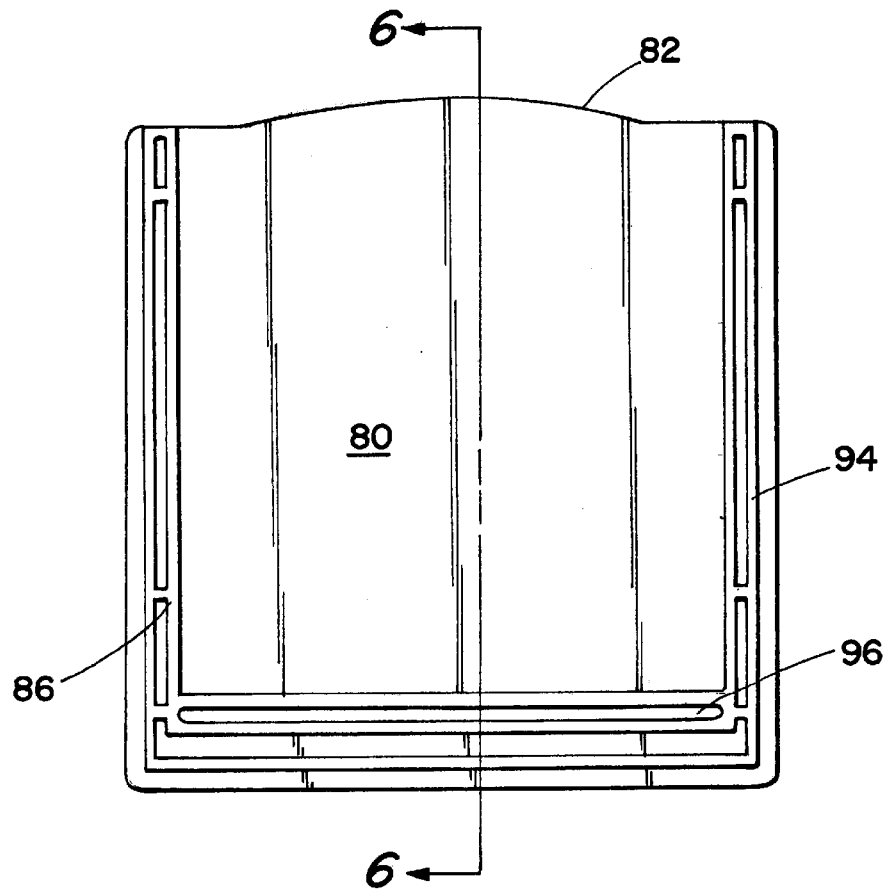
FIG. 5 is the front view of a gel cassette.
Figure 6:
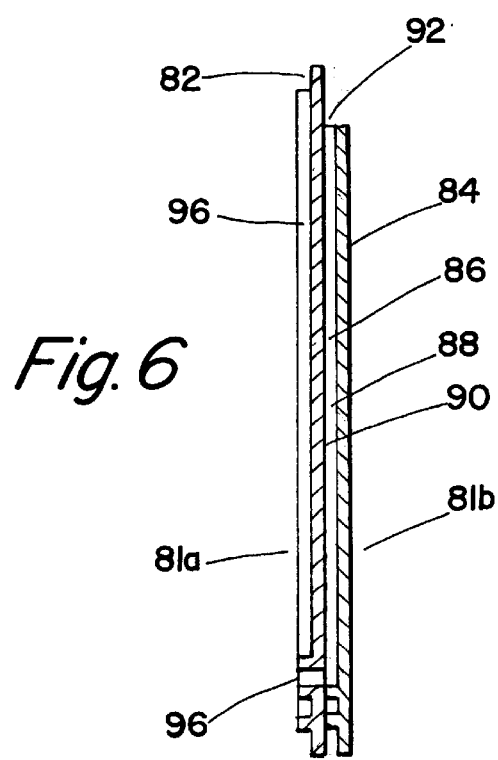
FIG. 6 is the cross-sectional view of the gel cassette taken from line 5—5 of FIG. 5.

As shown in FIGS. 1 and 2, buffer core body 41 includes an upper section 42 and a lower section 50. Upper section 42 generally resembles a U-shape, which is defined by a pair of spaced apart upraised members, left side member 42a and right side member 42b, and a horizontal member or beam 44, which forms the base of the upper or U-shape section 42. Located at the top portions of side members 42a and 42b are flanges 46a and 46b, respectively.

Traversing the side members 42a and 42b of the U-shaped section 42 is a first electrical conductor or wire 47, which is adaptable to receive an electrical charge. Wire 47 is connected to a male electrical pole conductor 49 that is affixed to flange 46b of side member 42b and extending downwardly therefrom (partially shown). Pole conductor 49 is adapted to fit into slot 32 of conductor strip 30 at the top portion of right side wall 16 of container 12, as shown in FIG. 1, and to establish conductivity with the strip.

The lower section 50 of buffer core body 41 has a left side column 58 and a right side column 60. The lower section also has a front inset 52 and a rear inset 54, which is defined by a recessed inset panel 56 positioned approximately half way between the front side and the back side of buffer core body 41. The inset panel 56 connects the left column 58 and the right column 60. It extends downwardly and curves away from the core body to form the base 64 of buffer core body 41. As seen in FIGS. 1–4, base 64 has a concave surface contour 63 on both the front side and the back side of buffer core body 41.

Buffer core body 41 has an inset opening 62 between horizontal member 44 and inset panel 56. A second electrical conductor comprising a thin wire 66 is provided to traverse the opening 62. Wire 66 is connected to a male electrical pole conductor 68 erected upon the flange 46a of the side member 42a of U-shaped section 42, which is adapted to conduct electrical current.

As shown in FIGS. 1–6, a gel cassette 80 is positioned on each of the front side and the rear side of the buffer core in a sandwiched fashion. Gel cassette 80 has a front surface 81a and the back surface 81b. It includes a pair of plates which are of thin wall construction. The plates are commonly referred to as the divider or divider plate 82 and retainer or retainer plate 84. Retainer plate 84 is slightly shorter in height than the divider plate 82.

Divider 82 is affixed to a peripheral ridge 86 along the lateral sides and the bottom periphery of retainer 84 to define an internal gel compartment 88 for holding an electrophoresis gel 90. As shown in FIGS. 1, 3, 4, 5 and 6, gel compartment 88 has a top or comb opening 92 at the top portion of the cassette for receiving a sample on which molecular separation takes place.

Side ridge 94, exterior to cassette 80, is provided along the lateral sides of divider plate 82. Side ridges 94 are spaced apart at a distance that approximates the distance between wall recess ridges 21 and 24 of container 12.

Located along the lower portion of divider plate 82 and traversing the width of the cassette 80 is a slot or opening 96 which opens gel compartment 88 to the exterior of the cassette 80.

Gel cassettes suitable for the present application are known in the art. In a typical gel cassette, the gel is pre-filled within the internal gel compartment for ease of handling. The top opening 92 is closed with a comb (not shown); and the slot 96 is masked closed with a removable tape (not shown). An example of the gel cassettes that are suitable for this application are the 12% Tris-glycine gels sold by Novel Experimental Technology of San Diego, Calif., under catalog No. EC6005. Gel cassettes of similar types are also commercially available from other firms.

As seen in FIGS. 1, 3 and 4, a gel cassette is positioned adjacent each of the front side 43 and the back side 45 of buffer core body 41 in a sandwiched fashion to define the well or upper chamber 48 with U-shaped section 42 for receiving a second buffer solution 98. As will be discussed in further detail below, the second buffer solution 98 is isolated from the first buffer 8 in container 12. In view of the isolation of the buffers, the portion of the container 12, which contains the first buffer solution 8, is often referred to as the lower chamber or lower buffer chamber, as being distinguished from the upper chamber or well 48. Thus the lower buffer chamber substantially comprises the front and rear chambers 26 and 28, and compartments 102 and 106, as seen in FIGS. 1, 3 and 4.

The two cassettes 80 also enclose the front inset 52 and the rear inset 54 to define the front compartment 102 and the rear compartment 106, respectively, which are in fluid communication with each other by way of the inset opening 62.

In the embodiment of the present invention, only approximately 10–15% of the upper portion of the gel cassettes 80 is positioned to partially form a portion of the sides of the well 48. Thus, the majority of the gel cassette is exposed to the first electrophoresis buffer solution.

Both the front and the rear surfaces of the buffer core body 41 are provided with grooves 71 and 73 for fitting and holding resilient strips 72 and 74, respectively, as a seal between the gel cassettes and the buffer core body. The seal ensures isolation of the buffer 98 in the well or upper chamber 48 from the front and rear compartments 102 and 106, and provides a cushion to reduce excess stress along the force bearing surfaces of the cassettes when they are held against the buffer core body.

The gel cassette at the front side of buffer assembly 40 is affixed in an elevated position relative to the lower periphery of buffer core base 64 to provide a lower opening 104 of buffer compartment 102 to permit passage of the first buffer solution between the compartment 102 and the front chamber 26 of container 12.

In the present embodiment, the cassette rests upon risers 76 at the buffer base 64. Other means, such as clamps, can also be used to affix the cassette in the elevated position so as to provide the opening to the buffer compartment 102.

In a similar fashion, the gel cassette at the back side of buffer core assembly 40 is also affixed at an elevated position relative to the base of the buffer core. In the present embodiment, risers 78 are provided at the buffer core base to elevate the cassette to define a lower opening 108 of the buffer compartment 106 to permit passage of the first buffer solution between the compartment 106 and the rear chamber 28 of container 12.

Prior to the use of cassette 80, the comb (not shown) and the tape (not shown) are removed. The sample to be analyzed is introduced into the gel compartment 88 through the comb opening 92 by appropriate means such as a pipette. The cassettes with their retainers proximal to the buffer core body 41 are held to rest upon the risers of the buffer core base 64. The buffer core assembly 40 is then slidably inserted into the left and right wall recesses 20 and 22 from the top of container 12 to rest upon its bottom 19. The buffer core assembly is then moved toward the front wall 14 of container 12 such that side ridges 94 of cassette divider plate 82 on the front side of the buffer core assembly are aligned coincidentally with and bear upon the wall recess ridges 21 and 24. This arrangement minimizes fluid flow between the lateral sides of cassette 80 between front chamber 26 and the wall recesses 20 and 22.

Although the above description refers to the use of two gel cassettes as part of the buffer core assembly, such reference should not be construed as a limitation with respect to the novelty associated with the use of the present invention or its functional characteristics when a single cassette is employed. Where it is only necessary to conduct a single electrophoresis run, a single cassette can be installed on one side of the body core, and a blank or a plate member can be placed on the other side to achieve similar performance and results with assured consistency and uniformity of temperature across the front and the back of the electrophoresis gel.

To secure the buffer core assembly in the container, a pair of wedge blocks are provided in the present embodiment. As shown in FIGS. 1 and 4, a lower wedge block 110 is disposed contiguous to cassette 80 at the back side 45 of buffer core assembly 40. The lower wedge block includes a generally square or rectangular front panel 112. On the lateral sides of the front panel, there are bearing surfaces 113a and 113b which are adapted to align with and to bear upon the side ridges 94 of the divider 82 of the gel cassette 80 and to hold it against the buffer core body.

In the embodiment as shown, bearing surfaces 113a and 113b are in the form of vertical side strips. This arrangement reduces fluid communication along the lateral sides of cassette 80 between rear chamber 28 and side wall recesses 20 and 22.

At the lower portion or the base 122 of front panel 112, a plurality of upraised push tabs 120 are provided to bear upon base 64 of buffer core body 41.

Affixed to the reverse side of front panel 112, a pair of spaced apart parallel side panels 116 and 118 are provided to enhance structural integrity of the lower wedge block 110 and to support it in an erect position. Side panels 116 and 118 are generally of the shape of a right-angled triangle with inclined edges 124a and 124b and vertical edges affixed to the front panel such that side panels 116 and 118 are in substantial alignment with the bearing surface or strip 113a or 113b, respectively.

The bases of the side panels 116 and 118 extend from panel 112 proximally to the back wall 18 of the container 12. The inclined edges or hypotenuses 124a and 124b of side panels 116 and 118 extend from the top to the base portion of lower wedge block 110.

As seen in FIGS. 1 and 4, an upper wedge block 126 superposed the lower wedge block 110. Upper wedge block 126 includes a top plate 128 which is adapted to rest upon the flange 38 of the walls of container 12 to cover substantially the rear top portion of container 12.

Top plate 128 has an opening 130 to accept a fitting 132, which includes a tubular member 134 for the delivery of the electrophoresis buffer 8 into the rear chamber 28. Tubular member 134 extends downwardly into the rear chamber with it opening 136 positioned slightly below the expected buffer fluid level to prevent splashing of the buffer when it is delivered into the container 12.

A second opening 138 is provided on the top plate 128 to permit access of temperature measuring instrumentation (not shown) into the rear chamber 28.

Affixed to top plate 128 is a pair of spaced apart parallel downwardly depending vertical side panels 140 and 142, which are aligned in a co-planer relationship with side panels 116 and 118, respectively, of the lower wedge block. Similar to side panels 116 and 118, panels 140 and 142 are generally of the shape of a right-angled triangle.

As shown in FIGS. 1 and 4, the vertical sides of the right-angled triangle of the side panels are positioned proximal to the rear wall of the container 12. A back panel 144 is affixed to top plate 128 and vertical side panels 140 and 142 to enhance the structural integrity of the upper wedge block.

The inclined edges or hypotenuses 146a and 146b of the panels 140 and 142 define the bearing edges which bear coincidentally upon the corresponding inclined edges 124a and 124b of side panels 116 and 118 of lower wedge block 110.

As shown in FIGS. 1 and 4, upper wedge block 126 is disposed above the lower wedge block 110 such that the inclined edges of the respective side panels of the upper wedge block and the lower wedge block are aligned coincidentally with each other. As upper wedge block 126 is lowered into container 12, each of the side panels 140 and 142 acts as a wedge between the back wall 18 and inclined edges 124a and 124b of the corresponding lower wedge block side panels such that the lower wedge block is displaced toward buffer core assembly 40.

As bearing surfaces 113a and 113b of lower wedge block 110 bear upon the cassette divider ridges 94, a bearing force is transmitted through the cassette 80 against the resilient strips 72 and 74 on buffer core body 41 to form a seal between the well 48 and the front and rear compartments 102 and 106. This ensures fluid and electrical isolation between the two buffers in container 12 and in the well or upper chamber 48 and to prevent mixing of the two buffer solutions, which can interfere with the proper molecular separation. It also reduces the risks of electrical grounding of the power supply or other sensitive instruments used in connection with the electrophoresis.

The resiliency of the strips 72 and 74 also provides a means of resistance against the bearing force of the wedge blocks such that a static balance is maintained among buffer core body 41, cassettes 80, the wedge blocks and the back wall 18 of the container 12, thereby securing them in container 12.

Lower wedge block 110 and upper wedge block 126 can be fabricated with a number of materials by a variety of methods. In the embodiment described herein, and by way of example only, they are formed by injection molding of acrylic plastic, adapted to be tolerant of a slight flex to effect the wedge action.

Container 12 is fitted with a lid 150, which is adapted to cover the top front portion of container 12 to prevent spillage or escape of the buffer out of the container. Lid 150 has an open box configuration inverted to seat upon the upper edge of the container walls.

Lid 150 has two top openings for mounting a pair of electrical conductor female plugs 152 and 154. Female plug 152 is aligned to receive the male conductor 34 on conductor strip 30 of the right side wall 16 of the container 12. Female plug 154 is aligned to receive the male conductor 68 of the buffer core body. Plugs 152 and 154 are electrically connected by suitable cables 164 and 166 which are adapted to receive an electrical current (or charges) from an appropriate power supply (not shown).

Lid 150 has a third top opening 156 to accept a tube fitting 158 which includes a tubular member 160. The tubular member extends downwardly into the front chamber 26 of container 12 with it opening 162 positioned slightly below the expected fluid level of buffer solution 8 to effect control of the buffer level, and to maintain it such that the buffer in the front chamber covers a substantial portion of the surfaces of gel cassettes 80 in which molecular separation occurs.

In application, buffer core assembly 40 and the wedge blocks 110 and 126 are first secured within container 12 in the manner as described above. Buffer solution 98 is dispensed into the well 48 above the top or comb openings 92 of the cassettes to establish fluid contact with gel 90 in the gel compartments. The buffer solution 8 is then introduced into container 12 until its level is approximately that of the horizontal member or beam 44.

Lid 150 is positioned above the front portion of container 12 such that the female electric plugs 152 and 154 are aligned with the pole conductors 34 and 68, respectively. As the lid is lowered onto the container 12, the female plugs are coupled with the pole conductors thereby also securing the lid to seat upon the top front portion of container 12.

After lid 150 is seated, conductor cables 164 and 166 are attached to a power supply system or charging means (not shown) for delivering an appropriate electrical charge to the electrophoresis system. In the embodiment of the present invention, cable 164 is connected to the power supply to deliver a negative charge, and cable 166 to deliver a positive charge. In practice, the polarity of the electrical charge can be reversibly applied to the buffers, as a matter of choice.

As electrical power is applied across pole conductors 34 (electrically coupled to conductor 49) and 68, an electrical potential is developed across wire 47 and wire 66. This in turn imposes an electrical potential between buffer solution 98, which is in contact with wire 47 in well 48, and buffer solution 8 as the latter is in contact with wire 66. Thus buffer 98 is negatively charged; and buffer solution 8 is positively charged.

As discussed above, gel 90 of cassettes 80 is in contact with buffer solution 98 in well 48 at the top cassette openings 92 and it is also in contact with the buffer solution in container 12 at the bottom slot 96. Therefore, the electrically charged buffers will result in an electrical field in gel 90 between the top opening 92 and the slot 96 to effect molecular separation of the electrophoresis experiment.

From the above discussions, it is apparent that the electrical charge is effectively applied to substantially the entire portion of the electrophoresis gel in the gel cassette where molecular separation is to occur.

Power supply systems or charging means suitable for use with the present invention are known in the art and are commercially available. So they are not described in details here.

As mentioned above, heat is generated during electrophoresis molecular separation as electrical charge is applied to the gel 90, thus creating uneven temperature gradients on the surfaces of the gel, as well as across its thickness. Such problem is effectively mitigated by controlling the surface temperature of the gel cassettes with the present invention.

While the electrophoresis buffer in container 12 serves as an electrical conducting anode, it also functions as a heat exchange medium or means to effect temperature control of the surface temperature of gel cassettes 80. Heat exchange between the buffer and the cassette surfaces is effected by circulating buffer 8 in contact with the surfaces of the cassettes 80 with appropriate heat transport means that are adaptable to maintain the buffer temperature and flow rate into and out of container 12 via tubular members 134 and 160, respectively.

Heat transport means for maintaining flow rates and temperatures for the electrophoresis buffer are known in the art and commercially available. Examples of such means are peristaltic pumps and jacket heat exchangers that are marketed by Novel Experimental Technology of San Diego, Calif., under the trademark Thermoflow, catalog No. EI8106. These means are not detailed here in the present discussion.

Buffer circulation to effect temperature control of the gel cassette surfaces and therefore the gel is initiated by a heat transport means (not shown) with the delivery of the electrophoresis buffer 8 via the tubular member 132 at a predetermined flow rate and temperature into the rear chamber 28 of the container 12. In application of the present embodiment, it has been shown that as little as 450 ml per minute of the buffer flow was sufficient to control the surface temperature differential of the cassettes in less than 0.1° C.

The flow path of the buffer solution 8 is established as it enters the space between front panel 112 of lower wedge block 110 and back panel 144 of upper wedge block 126. The buffer flow is directed to pass through opening 114 of front panel 112 of lower wedge block 110 and is projected onto the back side of buffer core assembly 40 where cassette 80 is secured. As a result, the outer surface of the divider 82 of cassette 80 on the back side of the buffer core assembly 40 is being washed continuously by the moving buffer whereby a heat exchange relationship is established between the buffer flow and the divider to maintain the surface temperature of the latter at a desired level. This in turn effectuates temperature control over gel 90 within cassette 80 since any temperature fluctuation can be eliminated by way of heat transfer with the buffer flow across the divider wall.

At the back side of buffer core assembly 40, the buffer flow is directed downwardly to enter rear compartment 106 through lower opening 108 where it is turned upwardly by the concave surface of the buffer core base 64. In the compartment 106, the buffer flow also establishes a heat exchange relationship with the surface of the retainer 84 of cassette 80 in a manner similar to that between the buffer flow and the outer surface of the divider 82 as discussed above.

In compartment 106, the buffer flow is directed to rise upwardly to reach the inset opening 62 where it is electrically charged by the conductor wire 66 before entering the front compartment 102. Passing through inset opening 62, the buffer flow is directed downwardly to enter the front compartment 102 and exit through the bottom opening 104 into the front chamber 26 while establishing fluid contact and similar afore-described heat exchange relationship with the surfaces of the retainer 84 and divider 82 of cassette 80 at the front side of the buffer core assembly.

As the buffer exits the bottom opening, its flow is diverted by the concave contour 63 of base 64 to turn toward the front portion of container 12 where the buffer flow moves upwardly. When the buffer level reaches the discharge opening 162 of the tubular member 160, it is evacuated and returned to the heat transport (exchange and pumping) means for temperature conditioning, where it is heated or cooled as required in order to maintain the temperature of the gel cassettes at the desired temperature.

Thus the design of the electrophoresis cell assembly of the present invention allows both sides of the cassette surfaces to be continuously exposed to the circulating buffer, which flows in a serpentine fashion in the container. Since both the surfaces of the divider plate and the retainer plate are in constant contact with the buffer flow, which is maintained at the desirable temperature, the electrophoresis gel that is sandwiched between the plates is also maintained at the desirable temperature.

The above-described invention can be applied to various electrophoretic applications including DNA sequencing, RNA or protein electrophoresis, isoelectric focussing, and electrophoretic transfer. In each case, the reproducible control of temperature throughout the run adds a desirable degree of control. Such control is particularly applicable where accurate, reproducible temperature control is a requirement, as in SSCP analysis.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An apparatus for conducting electrophoresis experiments comprising:
   (i) A container having a lower portion for receiving a first electrophoresis buffer solution and defining a lower chamber;
   (ii) A buffer core assembly immersable in the first buffer solution in the lower chamber, the buffer core assembly including:
      (a) a buffer core body having an upper section with upraised peripheral walls defining an upper chamber for receiving a second electrophoresis buffer solution isolated from the first buffer solution, and a lower section having a front inset, a rear inset and an inset opening adjacent the upper section, and
      (b) a pair of gel cassettes each containing an electrophoresis gel, the cassettes being securably affixed to the front and back sides of the buffer core body forming part of the peripheral walls of the upper chamber and having an opening to permit fluid communication with the second buffer solution contained therein, the cassettes further enclosing the front inset and the rear inset respectively to define a front compartment and a rear compartment in fluid communication with each other through the inset opening, each of the front compartment and the rear compartment having a lower opening to permit passage of the first electrophoresis buffer solution through the compartments; and
   (iii) Charging means electrically coupled to the first and second electrophoresis buffers to generate an electric field on the gel to effect molecular separation of an electrophoresis sample.

2. The invention according to claim 1 wherein the upper section of the buffer core body is generally of a U-shape.

3. The invention according to claim 1 wherein the charging means comprises:
   (i) a first electric conductor disposed within the inset opening to electrically couple the first buffer to the gel;
   (ii) a second electric conductor disposed within the upper chamber to electrically couple the second buffer to the gel; and
   (iii) a power supply to deliver electric charges to the conductors.

4. The invention according to claim 1 wherein the buffer core and the gel cassettes affixed thereto are securable to the container to define a front chamber and a rear chamber of the container and wherein buffer flow between the front and the rear chambers through the compartments is made in a serpentine fashion.

5. The invention according to claim 1 wherein the front surface and the rear surface of the cassettes are adapted to be in fluid contact with the first buffer in the container and with the buffer flow passing through the front and the rear compartments to define a heat transfer relationship between the first buffer and the front and rear surfaces of the cassettes.

6. The invention according to claim 1 wherein the buffer core further comprises resilient sealing means between the cassette and the buffer core to effect isolation between the well and the lower chamber.

7. The invention according to claim 1 which further comprises heat transport means for circulating the first buffer in the container to effect heat exchange between the gel cassettes and the buffer to effect temperature control over the surfaces of the gel cassettes.

8. The invention according to claim 7 wherein the heat transport means further comprises a pump and a heat exchanger for circulating the first buffer to and from the container.

9. The invention according to claim 1 which further comprises means to secure the gel cassettes to the buffer core.

10. The invention according to claim 1 wherein one of the gel cassettes is replaced by a blank.

11. An apparatus for conducting electrophoresis experiments comprising:
    (i) A container for receiving a first electrophoresis buffer solution;
    (ii) A buffer core immersable in the first buffer solution within the container, the buffer core having a U-shaped upper section and a lower section with a front inset, a rear inset and an inset opening adjacent the lower portion of the U-shaped section;
    (iii) A pair of gel cassettes each containing an electrophoresis gel, the cassettes being securably affixed to the front and back sides of the buffer core forming a well with the U-shaped section to receive a second buffer solution, and the cassette further enclosing the front inset and the rear inset respectively to define a front compartment and a rear compartment in fluid communication with each other through the inset opening, each of the front compartment and the rear compartment having a lower opening to permit passage of the first buffer solution through the compartments; and
    (iv) Charging means electrically coupled to the first and second buffers to generate an electric field on the gel to effect molecular separation of an electrophoresis sample.

12. The invention according to claim 11 wherein the passage of the first electrophoresis buffer solution through the compartments is made in a serpentine fashion.

13. The invention according to claim 11 wherein passage of the first electrophoresis buffer solution through the compartments is effected at a flow rate of no more than approximately 450 mls. per minute.

* * * * *